United States Defensive Publication [19] (H) [11] T978,003

Wu et al. [43] Jan. 2, 1979

[54] REDUCTION OF ASCORBIC ACID INTERFERENCE IN ASSAYS OF AQUEOUS FLUIDS

[76] Inventors: Tai-Wing Wu; Shirley S. Yau, both of Kodak Park Division, Rochester, N.Y. 14650

[21] Appl. No.: 879,573

[22] Filed: Feb. 21, 1978

[30] Foreign Application Priority Data

Jul. 11, 1977 [CA] Canada ..... 282481

[51] Int. Cl.[2] ..... C07G 7/02; G01N 31/14

[52] U.S. Cl. ..... 195/63; 195/66 R; 195/99; 195/103.5 R; 195/103.5 C

[57] ABSTRACT

Interference caused by ascorbic acid is eliminated by the presence of ascorbate oxidase in reagent compositions used in enzymatic assay of aqueous fluids such as blood serum for a specific analyte wherein the analyte is oxidized to peroxide and the peroxide reacts with an indicator to produce a detectable product. A preferred reagent composition contains an enzyme capable of catalyzing in the presence of oxygen the oxidation of the analyte to a peroxide, an indicator composition to produce a detectable product and ascorbate oxidase.

43 Claims, 1 Sheet Drawing,

41 Pages Specification

The file of this unexamined application may be inspected and copies thereof may be purchased (849 O.G. 1221, Apr. 9, 1968).

FIG. 1
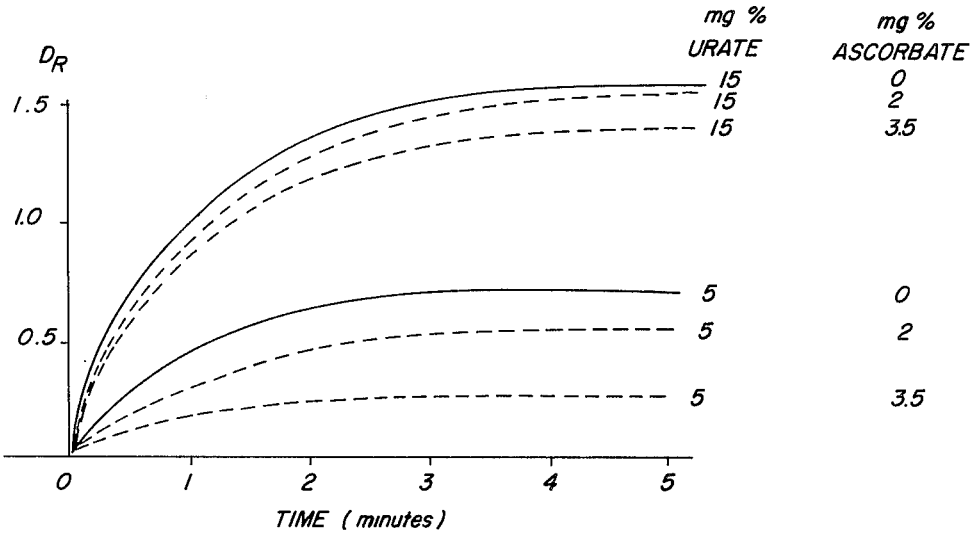
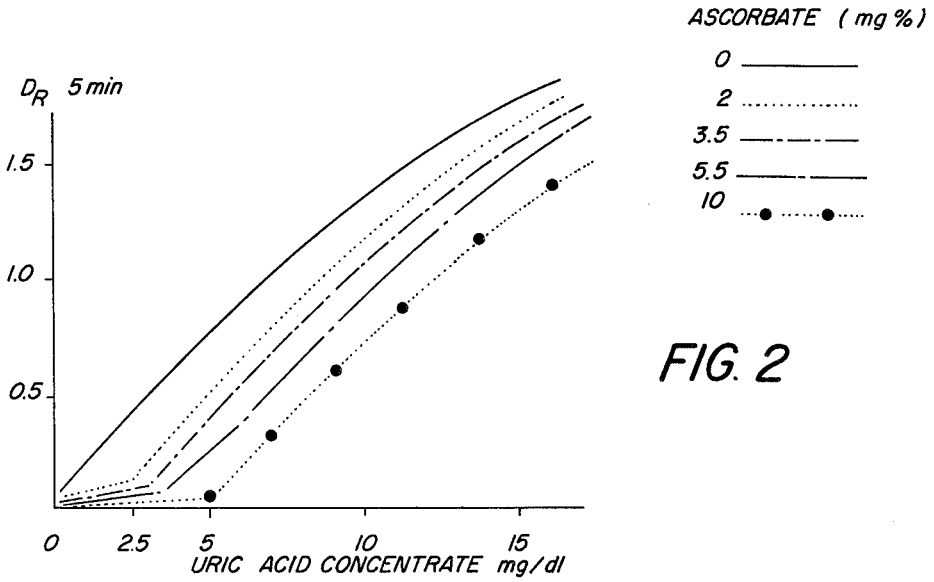
FIG. 2